United States Patent
Bok et al.

(10) Patent No.: US 7,192,981 B2
(45) Date of Patent: Mar. 20, 2007

(54) 3,4-DIHYDROXYHYDROCINNAMIC ACID DERIVATIVE

(75) Inventors: Song-Hae Bok, Taejon (KR); Eun-Eai Kim, Taejon (KR); Sang-Ku Lee, Taejon (KR); Ji-Won Yoon, Vernon Hills, IL (US); Hee-Sook Jeon, Lake Bluff, IL (US); Lee-Yong Khil, Calgary (CA); Wi Kim, Toronto (CA)

(73) Assignee: Bionutrigen Co., Ltd. (KR)

( * ) Notice: Subject to any disclaimer, the term of this patent is extended or adjusted under 35 U.S.C. 154(b) by 0 days.

(21) Appl. No.: 11/079,888

(22) Filed: Mar. 14, 2005

(65) Prior Publication Data

US 2006/0205813 A1    Sep. 14, 2006

(51) Int. Cl.
  *A61K 31/235*  (2006.01)
  *C07C 69/76*   (2006.01)
(52) U.S. Cl. .......................... 514/543; 560/75; 514/532
(58) Field of Classification Search ............... 514/532, 514/543; 560/98, 75
  See application file for complete search history.

(56) References Cited

OTHER PUBLICATIONS

Etzenhouser et al , Mechanism of toxicity of esters of Caffeic and dihydrocaffeic acids, 2001, Bioorganic & Medicinal Chemistry, 9 (1), 199-209, (p. 1).*

* cited by examiner

Primary Examiner—Taylor Victor Oh
(74) Attorney, Agent, or Firm—Buchanan Ingersoll & Rooney PC (57) ABSTRACT

According to the invention, there is provided a novel 3,4-dihydroxyhydrocinnamic acid derivative, designated DHH105, having blood glucose lowering effects in vivo as a result of the enhancement of glucose transport mediated by the increase of insulin receptor signaling.

This invention thus relates to a 3,4-dihydroxyhydrocinnamic acid derivative useful as an anti-diabetic agent, represented by the following formula I:

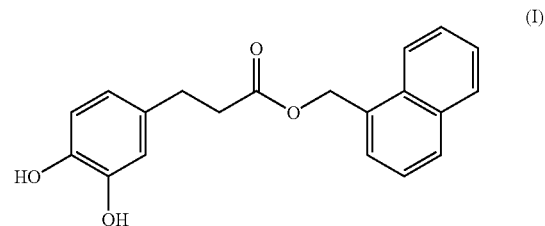

or pharmaceutically acceptable salts thereof, to a method for preparing the compound, and to a composition for treating diabetes comprising the same as an active ingredient.

3 Claims, 6 Drawing Sheets

3,4-DIHYDROXYHYDROCINNAMIC ACID DERIVATIVE

FIELD OF THE INVENTION

The present invention relates to a novel 3,4-dihydroxyhydrocinnamic acid derivative, designated DHH105, useful as an anti-diabetic agent, represented by the following formula I:

or pharmaceutically acceptable salts thereof, to a method for preparing the compound, and to a composition for treating diabetes comprising the same as an active ingredient.

BACKGROUND OF THE INVENTION

Type 2 diabetes is characterized by abnormal glucose homeostasis, resulting in hyperglycemia, and is associated with microvascular, macrovascular, and neuropathic complications. Thus, the regulation of blood glucose is the major target for the management of type 2 diabetes, which can prevent the development of complications and improve the quality of life.

In type 2 diabetes, hyperglycemia results from metabolic abnormalities including insulin resistance, defects in glucose-stimulated insulin secretion, and excessive hepatic glucose output (1). In most genetically predisposed individuals, there is a slow progression from a normal state to insulin resistance, hyperinsulinemia, glucose desensitization, defects in insulin secretion, impaired glucose tolerance, and then to hyperglycemia (2).

Impaired glucose transport is one of the major factors contributing to insulin resistance in type 2 diabetic patients (3). The ability of insulin to mediate tissue glucose uptake is a critical step in maintaining glucose homeostasis and in clearing the post-prandial glucose load (4,5). Glucose transport is mediated by specific carriers called glucose transporters (GLUTs), and insulin-stimulated glucose transport is mediated largely by GLUT4 (6). Binding of insulin to its receptor activates the receptor's tyrosine kinase activity, which phosphorylates a number of downstream substrates such as insulin receptor substrate-1 (IRS-1) and IRS-2. Phosphorylated IRS-1 and -2 bind to a variety of other substrates and trigger insulin action, such as glucose uptake (7,8).

Herbal plants have been used for medicinal purposes for centuries. For example, Cinnamon, widely consumed as a beverage in Asian countries, is known to have a glucose lowering effect (9,10) and prevent type 2 diabetes (11). And it was shown that the basal and insulin-stimulated glucose uptake of rat adipocytes was increased by green tea (12).

Pharmacological agents that enhance glucose transport are useful for lowering blood glucose levels in type 2 diabetic patients. In the present invention, the present inventors synthesized small molecules based on the anti-diabetic components of cinnamon and screened them for glucose transport activity. One of these, an ester derivative of 3,4-dihydroxyhydrocinnamic acid, designated DHH105, most significantly increased glucose transport. And the present inventors found out that the compound is very useful as an anti-diabetic agent, since the compound has blood glucose lowering effects in vivo as a result of enhancing insulin signaling and subsequent glucose transport.

SUMMARY OF THE INVENTION

According to the invention, there is provided a novel 3,4-dihydroxyhydrocinnamic acid derivative, designated DHH105, having blood glucose lowering effects in vivo as a result of enhancing insulin signaling and subsequent glucose transport. This invention thus relates to a 3,4-dihydroxyhydrocinnamic acid derivative useful as an anti-diabetic agent, represented by the following formula I:

or pharmaceutically acceptable salts thereof, to a method for preparing the compound, and to a composition for treating diabetes comprising the same as an active ingredient.

DETAILED DESCRIPTION OF THE INVENTION

The present invention provides a novel 3,4-dihydroxyhydrocinnamic acid derivative, designated DHH105, useful as an anti-diabetic agent, represented by the following formula I:

(I)

or pharmaceutically acceptable salts thereof, to a method for preparing the compound, and to a composition for treating diabetes comprising the same as an active ingredient.

The present invention also provides a method for preparing 3,4-dihydroxyhydrocinnamic acid naphthalene methyl ester, characterized by comprising esterification of 3,4-dihydroxyhydrocinnamic acid with 1-(chloromethyl)naphthalene.

Finally, the present invention provides a pharmaceutical composition for treatment and prevention of diabetes comprising 3,4-dihydroxyhydrocinnamic acid naphthalene methyl ester or pharmaceutically acceptable salts thereof as an active ingredient.

The compound of the invention, 3,4-dihydroxyhydrocinnamic acid naphthalene methyl ester (DHH105), has blood glucose lowering effects in vivo as a result of enhancing insulin signaling and subsequent glucose transport. Thus, the compound is useful as an anti-diabetic agent.

In this disclosure, the term "DHH105" refers to 3,4-dihydroxyhydrocinnamic acid naphthalene methyl ester.

In the present invention, DHH105 was identified as having an anti-diabetic effect and the mechanisms by which it lowers blood glucose, were examined.

First, the effect of DHH105 on the non-fasting blood glucose level in ob/ob mice, an animal model of type 2 diabetes, was examined in vivo. And it was found that blood glucose levels were significantly decreased in DHH105-treated ob/ob mice as compared with untreated vehicle control ob/ob mice. It was also found that DHH105 treatment decreased blood glucose levels in a chemically induced diabetic C57BL/6 mice, in which insulin-producing pancreatic β cells have been destroyed by treatment with STZ. This result suggests that the blood glucose-lowering effect of DHH105 may result from increased glucose disposal from peripheral tissues, regardless of their interaction with insulin. There were no differences in body weight between DHH105-treated and untreated mice. In addition, no gross lesions of the liver were observed, suggesting that there are no apparent side-effect of DHH105 treatment.

And the effect of DHH105 on glucose transport was examined in isolated rat epididymal adipocytes, since impaired glucose transport is one of the major factors contributing to insulin resistance in diabetic patients. It was found that DHH105 increased glucose transport in adipocytes in a dose- and time-dependent manner and showed a maximum effect at 500 μM when adipocytes were treated for 4 h. DHH105 increased the $V_{max}$ (which indicates the number of carriers on the cell surface) by three times as compared to that of basal glucose transport, whereas the $K_m$ (which indicates the affinity of a carrier for its substrate) was not changed. DHH105 showed the highest effect on glucose transport as compared with known anti-diabetic drugs such as troglitazone, metformin, and glyburide.

And it was examined whether DHH105 exerts its action by binding to the insulin receptor. It was found that DHH105 competed with insulin for binding to the insulin receptor. Competition of binding site with insulin can either stimulate or inhibit insulin signal transduction. However, DHH105 did not affect insulin-stimulated glucose transport, suggesting that DHH105 does not inhibit or sensitize insulin action. It was also found that DHH105 treatment phosphorylates IR-β and IRS-1 and activates PI3-kinase, and treatment with a PI3-kinase inhibitor such as LY294002 significantly reduced glucose transport in adipocytes. These results suggest that DHH105 activates the insulin receptor signaling pathway, contributing to the enhancement of GLUT4 translocation.

DHH105 binds to insulin receptors and activates the insulin signal transduction pathway, subsequently increasing the translocation of GLUT4 and contributing to the increased clearance of peripheral glucose. Because the blood glucose-lowering effect of DHH105 can be achieved without insulin and DHH105 does not sensitize insulin action, DHH105 might have therapeutic potential as an anti-diabetic drug in the presence or absence of insulin with less risk of hypoglycemia.

The present invention is explained in detail by the following examples. However, the examples are provided for illustration of the present invention not for limitation thereof.

In examples, the statistical significance of the differences between groups was analyzed by Student's t test. A level of P<0.05 was accepted as significant.

EXAMPLE 1

Synthesis and Identification of DHH105.

3,4-dihydroxyhydrocinnamic acid naphthalene methyl ester was prepared by esterification of 3,4-dihydroxyhydrocinnamic acid with 1-(chloromethyl)naphthalene using NaHCO$_3$ and KI in N,N-dimethylformamide. The detail is given below.

6.0 g (32.9 mmol) of 3,4-Dihydroxyhydrocinnamic acid was dissolved in 30 mL of N,N-dimethylformamide, and 6.0 g (33.9 mmol) of 1-(chloromethyl)naphthalene, 4.2 g (50.0 mmol) of NaHCO$_3$ and 6.0 g (36.1 mmol) of KI were added successively. The reaction mixture was stirred at 80° C. for 3 hours, cooled to room temperature, diluted with 200 mL of water, and extracted with 300 mL of ethyl acetate. The extracts were washed with 200 mL of water and 300 mL of brine, dried over anhydrous MgSO$_4$, and concentrated under reduced pressure. The residue was purified by column chromatography on silica gel (4:1 hexane-EtOAc) to afford 8.2 g (77% yield) of DHH105 as a pale yellow syrup:

$^1$H NMR (CD$_3$OD, 400 MHz) δ (ppm) 7.88 (m, 2H), 7.84 (dd, J=7.2, 2.8 Hz, 1H), 7.51 (m, 2H), 7.43 (d, J=2.0 Hz, 1H), 7.42 (d, J=7.2 Hz, 1H), 6.621 (d, J=2.0 Hz, 1H), 6.62 (d, J=8.0 Hz, 1H), 6.45 (dd, 8.0, 2.0 Hz, 1H), 5.52 (s, 2H), 2.77 (t, J=6.8 Hz, 2H), 2.60 (t, J=6.8 Hz, 2H); $^{13}$C NMR (CD$_3$OD, 100 MHz) δ (ppm) 173.5, 145.1, 143.5, 134.0, 132.2, 131.74, 131.68, 129.0, 128.4, 127.2, 126.4, 125.8, 125.1, 123.4, 119.4, 115.3, 115.2, 64.4, 36.1, 30.3.

EXPERIMENTAL EXAMPLE 1

Glucose Tolerance Tests.

Male C57BL/6 and C57BL/6 ob/ob mice were purchased from The Jackson Laboratory (Bar Harbor, Me.), and Sprague-Dawley (SD) rats were purchased from Charles River Laboratories (Wilmington, Mass.). The animals were maintained and bred under specific pathogen-free conditions and provided with sterile food and water ad libitum at the Animal Resources Centre, Faculty of Medicine, University of Calgary. The use and care of the animals used in this study were approved by the Animal Care Committee, Faculty of Medicine, University of Calgary.

DHH105 was dissolved in DMSO and emulsified in olive oil (1:50 v/v). DHH105, at a dose of 150 mg/kg body weight (b.w.) in 100 μl, was injected intraperitoneally (i.p.) every day into diabetic ob/ob mice (blood glucose level>230 mg/dl) and STZ-treated diabetic C57BL/6 mice (blood glucose level>300 mg/dl). Control mice received the same amount of olive oil without DHH105. Blood glucose levels were measured with a glucometer (One Touch Ultra, Lifescan, Milpitas, Calif.) every morning between 9:00–10:00 a.m. just before injection of DHH105.

To determine whether treatment with DHH105 can decrease the blood glucose level in STZ-induced diabetic C57BL/6 mice (blood glucose levels>300 mg/dl), mice were treated with DHH105 (150 mg/kd) daily for 2 weeks. Glucose tolerance tests were performed at 2 weeks after the treatment with DHH105. Briefly, mice were fasted overnight and injected with glucose (2 g/kg b.w., i.p.). Blood glucose levels were measured at 0, 15, 30, 60, and 120 min after glucose injection.

Figure 1:
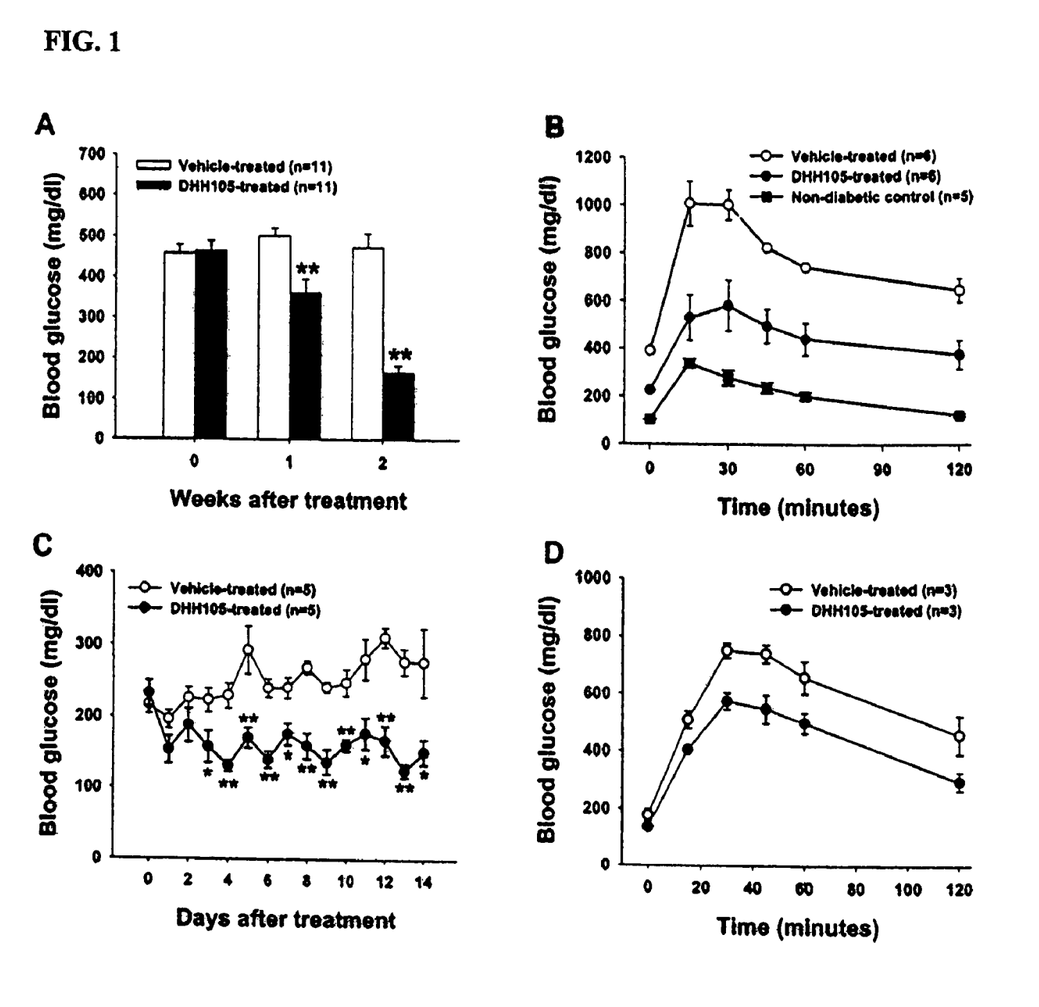
FIG. 1 shows effect of 3,4-dihydroxyhydrocinnamic acid naphthalene methyl ester, designated DHH105 treatment on blood glucose levels in diabetic mice (A, B: STZ-induced diabetic C57BL/6 mice, C, D: diabetic ob/ob mice)
Figure 2:
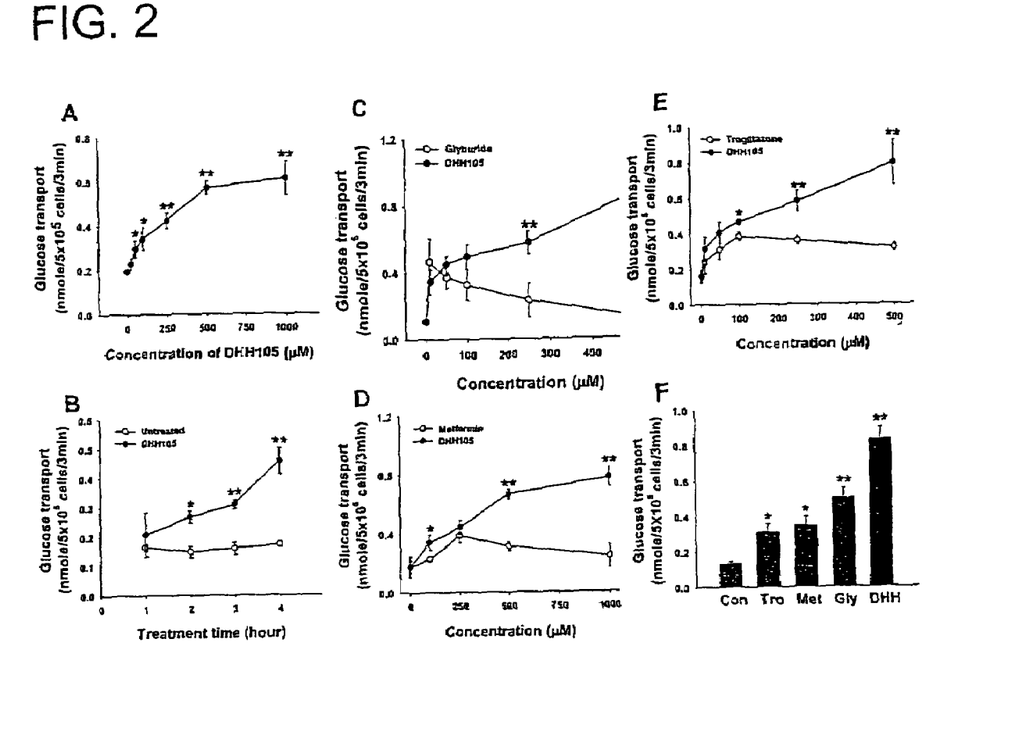
FIG. 2 shows effect of DHH105 treatment on glucose transport in isolated rat epididymal adipocytes (A: treatment with the indicated concentrations of DHH105 for 4 h, B: treatment with DHH105 (500 μM) for the indicated times, C: treatment with the indicated concentration of glyburide for 4 h, D: treatment with metformin, E: treatment with troglitazone, F: treatment with DHH105 (500 μM; DHH), glyburide (25 μM; Gly), metformin (250 μM; Met), or troglitazone (100 μM; Tro) for 4 h and untreated adipocytes were used as a control)

In result, blood glucose levels were significantly decreased at 2 weeks after treatment (FIG. 2A). When the glucose clearance was examined by GTT in DHH105-treated mice, it was found that DHH105 treatment significantly improved glucose clearance after artificial glucose loading as compared with untreated diabetic control mice (FIG. 2B). The blood glucose lowering effect was further determined in ob/ob mice, a model of type 2 diabetes. Diabetic ob/ob mice (blood glucose levels>230 mg/dl) were treated with DHH105 (150 mg/kg) daily for 2 weeks, and blood glucose levels were examined. In result, the blood glucose levels began to decrease at 4 days after first injection of DHH105 (FIG. 2C). Although blood glucose levels of all mice fluctuated during the experiment, the blood glucose levels of the treated mice remained significantly lower than those of vehicle-treated control mice. Glucose clearance was also significantly improved in DHH105-treated ob/ob mice (FIG. 2D).

EXPERIMENTAL EXAMPLE 2

Glucose Transport Assay.

To examine the effect of DHH105 on glucose transport, isolated adipocytes from 5 week-old SD rats were treated with various concentrations of DHH105 and 2-DOG uptake was measured.

Epididymal adipose tissue was removed from 5 week-old SD male rats and digested with collagenase type II (1 mg/ml; Sigma Chemical Co., St. Louis, Mo.) in 1 ml Krebs-Ringer HEPES (KRH) buffer (131 mM NaCl, 4.7 mM KCl, 2.5 mM CaCl$_2$, 1.25 mM MgCl$_2$, 2.5 mM NaH$_2$PO$_4$, 10 mM HEPES, pH 7.4) supplemented with 1% bovine serum albumin and 2 mM pyruvate for 1 h at 37° C. After digestion, adipocytes were separated by gentle massage with a rubber policeman followed by sieving through a 200 μm polypropylene mesh. Isolated adipocytes were washed with fresh KRH buffer without collagenase three times. Adipocytes were counted under the microscope.

Isolated adipocytes (3–4×10$^5$ cells/ml) in KRH buffer were incubated at 37° C. for 20 min in a shaking water bath. Adipocytes were then treated with DHH105 (500 μM or as indicated). To determine whether GLUT4 is involved in glucose transport, phenylarsine oxide (PAO, 1 μM; Sigma) was added 10 min prior to the addition of DHH105. To examine whether phosphatidylinositol 3-kinase (PI3-kinase) is involved in glucose transport, the PI3-kinase inhibitor, LY294002 (50 μM; Sigma) or wortmannin (100 nM; Sigma) was added 10 min prior to the addition of DHH105, and cells were incubated for 4 h. After incubation, [$^3$H]-2-deoxyglucose (2-DOG; 0.5 μCi, 0.125 mM; Amersham Pharmacia Biotech, Buckinghamshire, UK) was added and the cells were incubated for 3 min. Three hundred μl of cell suspension was transferred to microtubes containing 100 μl of silicone oil (Sigma). Cells were centrifuged for 30 sec, the oil layer was removed, and the radioactivity in the cell layer was measured. Trapped [$^3$H]-2-DOG on the outer surface of the adipocytes was measured in the presence of 1.2 mM phloretin (Sigma) and the radioactivity was subtracted from that of the sample. To determine the kinetics of glucose transport, various concentrations of 2-DOG (0.125 to 10.0 mM) were used.

Figure 3:
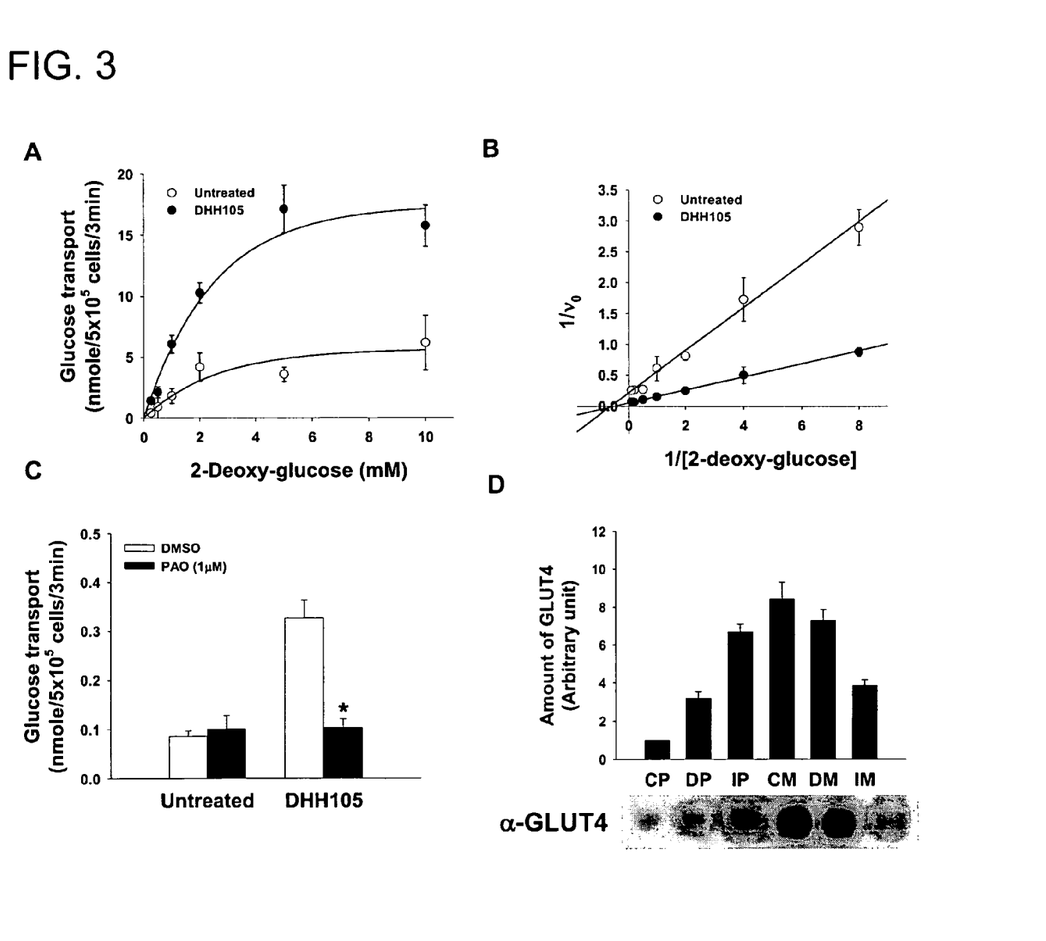
FIG. 3 shows effect of DHH105 treatment on GLUT4 translocation in adipocytes (A: treatment with DHH105 (500 μM) for 4 h. Glucose transport was measured in the presence of the indicated concentrations of 2-DOG and the results were plotted using the Michaelis-Menten, B: The results were plotted using the Lineweaver-Burk equations, C: treatment without (Untreated) or with DHH105 (500 μM) for 4 h in the presence or absence of PAO (1 μM), D: treatment with 500 μM DHH105 for 4 h or insulin (25 ng/ml) for 30 min.)

In result, 2-DOG uptake gradually increased with DHH105 treatment in a dose-dependent manner and peaked at a concentration of 500 μM DHH105 (FIG. 3A). And when the effect of DHH105 on glucose uptake during various incubation times was examined, it was found that treatment with 500 μM DHH105 resulted in increased 2-DOG uptake from 1 h and 2-DOG uptake gradually increased in a time-dependent manner (FIG. 3B). These results suggest that DHH105 treatment increases glucose transport in a dose- and time-dependent manner.

When isolated SD rat adipocytes were treated with various concentration of DHH105, glyburide, metformin, or troglitazone and 2-DOG uptake was measured to compare the effect of DHH105 on glucose transport with that of known anti-diabetic drugs, DHH105 showed a significantly higher effect on glucose transport in a dose-dependent manner as compared with other anti-diabetic drugs at doses of 500 μM or more (FIG. 3C–E). In contrast, the other anti-diabetic drugs showed increased glucose transport only at lower doses, whereas at higher doses glucose transport decreased (glyburide, FIG. 3C) or remained unchanged (metformin, FIG. 3D; troglitazone, FIG. 3E). When the effect of these drugs at their optimum concentrations was compared, it was found that DHH105 increased glucose transport 4-fold, whereas the other anti-diabetic drugs increased glucose transport 2-fold to 2.5-fold as compared with the untreated control (FIG. 3F).

Figure 4:
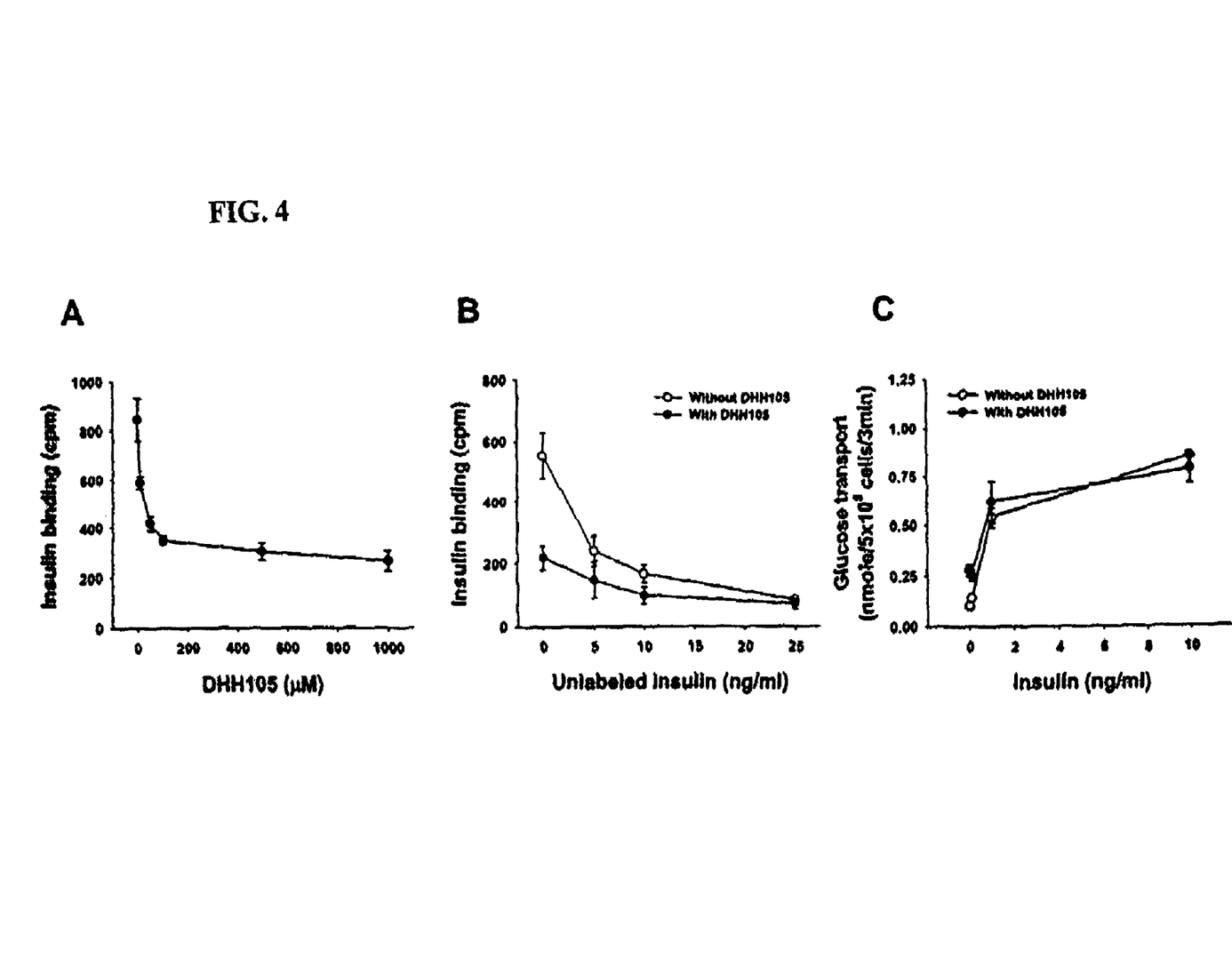
FIG. 4 shows effect of DHH105 on insulin receptor (A: treatment with DHH105 and [$^{125}$I]-insulin (0.1 ng/ml) for 2 h, B: treatment with insulin and [$^{125}$I]-insulin (0.1 ng/ml) in the presence or absence of 500 μM DHH105 for 2 h, C: treatment with 500 μM DHH105 for 3.5 h and the indicated concentrations of insulin for 30 min)

And the results of 2-DOG uptake were plotted according to the Michaelis-Menten equation (FIG. 4A) and transformed by Lineweaver-Burk plot (FIG. 4B).

When the Vmax and Km values were calculated from the Lineweaver-Burk equation, it was found that the $V_{max}$ of glucose transport in DHH105-treated adipocytes was 3-fold higher as compared with that in untreated control adipocytes without DHH105 treatment (5.56±0.02 vs 17.14±0.25 mmol/3 min), whereas there was no difference in Km value between DHH105-treated and control adipocytes (1.76±0.04 vs 1.78±0.38 mM). These results indicate that DHH105 may increase the amount of glucose transporters in the plasma membrane.

When 2-DOG uptake was measured in the presence of PAO (1 μM), which is known to inhibit GLUT4-mediated transport in adipocyte, to investigate whether GLUT4 is involved in DHH105-induced glucose transport, it was found that PAO completely abolished glucose transport induced by DHH105 (FIG. 4C). These results suggest that GLUT4 is involved in the increase of glucose transport by DHH105 treatment.

When cell lysates prepared from DHH105-treated adipocytes were fractionated and the amount of GLUT4 in the plasma and microsomal membrane fractions was measured by western blot using anti-GLUT4 antibody, to examine whether DHH105 treatment increases the translocation of GLUT4 to the plasma membrane, it was found that immunoreactive GLUT4 in the plasma membrane fraction was increased in DHH105-treated adipocytes as compared with untreated control adipocytes, whereas the amount of GLUT4 in the microsomal membrane fraction was decreased (FIG. 4D). These results indicate that DHH105 increases the translocation of GLUT4 from microsomal membrane to the plasma membrane in adipocytes.

EXPERIMENTAL EXAMPLE 3

Insulin Binding Assay.

To examine whether DHH105 binds to the insulin receptor and activates the insulin signal transduction pathway, [$^{125}$I]-insulin binding to adipocytes was measured in the presence of DHH105.

Isolated adipocytes were incubated in KRH buffer for 1 h to remove residual insulin. Adipocytes were then washed three times and resuspended in KRH buffer. Adipocytes ($2 \times 10^5$ cells/vial) were incubated with DHH105 or insulin in the presence of [$^{125}$I]-insulin (0.1 ng/ml; Perkin-Elmer Life and Analytical Sciences, Downers Grove, Ill.) for 2 h at 16° C. in a shaking bath. To measure non-specific binding, 50 μg of unlabelled insulin (Sigma) were added to cells along with [$^{125}$I]-insulin. After incubation, adipocytes were harvested by silicon oil and the radioactivity was measured.

Figure 5:
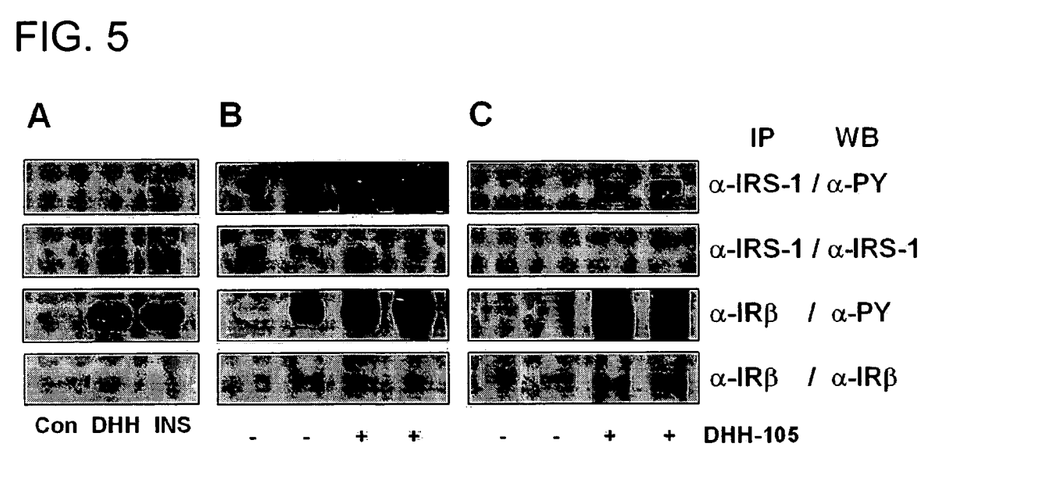
FIG. 5 shows effect of DHH105 on phosphorylation of IR-β and IRS-1 (A: untreated control, B: STZ-induced diabetic C57BL/6 mice, C: ob/ob diabetic mice at 2 weeks after treatment with DHH105)

In result, addition of DHH105 inhibited the binding of [$^{125}$I]-insulin to adipocytes (FIG. 5A) and addition of DHH105 together with insulin further inhibited binding (FIG. 5B). These results indicate that DHH105 competes with [$^{125}$I]-insulin for binding sites on adipocytes.

When glucose transport was examined after treatment with insulin in the presence or absence of DHH105, to determine whether DHH105 affects insulin-stimulated glucose transport, it was found that insulin treatment increased glucose transport in a dose-dependent manner, however, DHH105 treatment did not influence the effect of insulin on glucose transport (FIG. 5C). This result indicates that DHH105 does not inhibit or sensitize the effect of insulin on glucose transport.

EXPERIMENTAL EXAMPLE 4

Immunoprecipitation and Immunoblotting Assay.

(Subcellular Fractionation of Adipocytes)

Adipocytes treated with DHH105 for 4 h or insulin for 30 min were washed three times with HES buffer [8 mM HEPES, 250 mM sucrose, 2 mM EDTA, 20 mM NaF, 50 mM NaVO4, 50 mM sodium pyrophosphate, protease inhibitor cocktail (Sigma), and phosphatase inhibitor cocktail (Sigma), pH 7.4]. Adipocytes were homogenized in 20 ml HES buffer with a potter Elvehjem teflon pestle (15 strokes). Homogenates were centrifuged at 1000 g for 10 min and the supernatant was centrifuged again at 16,000 g for 20 min. The resulting pellet was resuspended in 500 μl HES buffer, carefully laid on a discontinuous sucrose gradient (density top to bottom: 1.0592, 1.1270, 1.1533, 1.1764, 1.2575) and centrifuged at 110,000 g for 70 min. The plasma membrane fraction was obtained from the gradient density of 1.1533, diluted in 50 ml HES buffer, and centrifuged at 16,000 g for 20 min. The pellet (plasma membrane fraction) was resuspended in 500 μl HES buffer and stored at −70° C. To obtain the microsomal membrane fraction, the supernatant from the second centrifugation was centrifuged at 220,000 g for 70 min. The pellet was washed, resuspended in 500 μl HES buffer and stored at −70° C. The protein content of each fraction was measured by the Bradford method.

(Immunoprecipitation)

Adipocytes treated with DHH105 for 2 h or insulin for 10 min were homogenized in 5 ml lysis buffer (20 mM Tris, pH 7.4, 1% SDS, 10% glycerol, 150 mM NaCl, 2 mM EDTA, 20 mM NaF, 1 mM NaVO4, 2 mM sodium pyrophosphate, protease inhibitor cocktail, and phosphatase inhibitor cocktail) with a teflon pestle (15 strokes). Homogenized adipocytes were sonicated for 3 min and solubilized for 30 min. The homogenate was centrifuged at 3,000 g for 10 min at 4° C. The protein concentration of the lysate was determined by the Bradford method. After dilution (1 μg/μl protein concentration), the lysates were incubated with anti-insulin receptor-β (IR-β) antibody (Upstate Biotech, Charlottesville, Va.) or anti-IRS-1 antibody (Upstate Biotech) overnight at 4° C. Protein A Sepharose beads (100 μl, Amersham Pharmacia Biotech) were added and the mixture was gently rocked for 2 h at 4° C. After centrifugation at full speed in a microcentrifuge for 5 min at 4° C., the pellet was washed and suspended in 2× sample buffer (50 mM Tris-HCl, pH 6.8, 10% glycerol, 2% SDS, 0.1% bromophenol blue, 5% β-mercaptoethanol) and boiled.

(Immunoblotting)

Proteins were separated by 10% SDS-PAGE and transferred to a polyvinyl difluoride membrane (Amersham Pharmacia Biotech). After transfer, the membranes were blocked with 5% skim milk in Tris-buffered saline with Tween 20 (TBST; 0.05% Tween 20, 200 mM Tris-HCl, 500 mM NaCl, pH 7.5) for 1 h at room temperature. The membranes were incubated with anti-IR-β, anti-IRS-1, anti-phosphotyrosine, or anti-p85 PI3-kinase (Upstate Biotech); anti-Akt/PKB or anti-phospho-Akt/PKB (Cell Signalling Technology, Beverly, Mass.); anti-GLUT4 (Santa Cruz Biotechnology Inc., Santa Cruz, Calif.); or anti-β actin (Sigma) antibody in 5% bovine serum albumin in TBST for 1 h at room temperature or overnight at 4° C. After washing, the membranes were incubated with secondary antibodies labeled with horseradish peroxidase (HRP) in 5% skim milk in TBST for 1 h. The membranes were washed and the immunoreactive proteins were detected with an enhanced chemoluminescence western blot detection kit (Amersham Pharmacia Biotech).

(Phosphorylation of IR-β and IRS-1)

Figure 6:
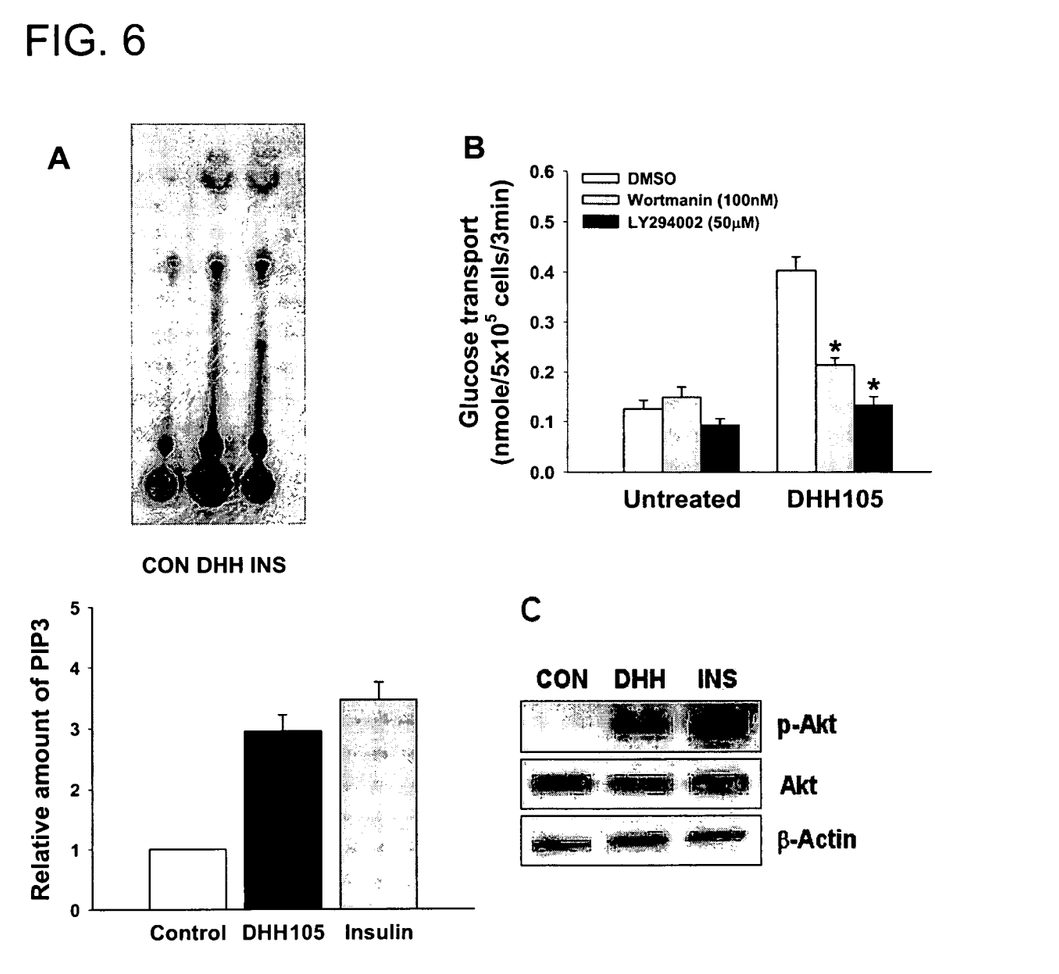
FIG. 6 shows effect of DHH105 on PI3-kinase activity and Akt/PKB phosphorylation, contributing to glucose transport (A: treatment with 500 μM DHH105 (DHH) for 2 h or 25 ng/ml insulin (INS) for 10 min, B: treatment with DHH105 (500 μM) for 4 h in the presence or absence of LY294002 (50 μM) or wortmannin (100 nM), C: treatment with 500 μM DHH105 for 4 h or 25 ng/ml insulin for 30 min).

To examine whether DHH105 treatment increases autophosphorylation of the insulin receptor and its tyrosine kinase activity, the phosphorylation of IR-β and IRS-1 were measured by immunoprecipitation and western blot in DHH105-treated adipocytes from SD rats. The phosphorylation was increased in DHH105-treated adipocytes, similar to insulin-treated adipocytes, as compared with the untreated control (FIG. 6A).

To examine whether in vivo treatment of STZ-induced diabetic C57BL/6 mice or ob/ob mice with DHH105 also increases phosphorylation of IR-β, and IRS-1, fat tissue was removed from the mice after 2 weeks of DHH105 treatment and phosphorylation of IR-β and IRS-1 was measured by immunoprecipitation and western blot. Consistent with the in vitro results, DHH105 treatment increased phosphorylation of IR-β and IRS-1 in adipose tissue from STZ-induced diabetic C57BL/6 mice (FIG. 6B) and ob/ob mice (FIG. 6C).

EXPERIMENTAL EXAMPLE 5

PI3-Kinase Assay.

Phosphatidylinositide (PI) in DMSO (1 mg/ml) was mixed with an equal volume of buffer A (10 mM HEPES, 100 mM NaCl, 1 mM EGTA, 0.03% NP-40, pH 7.0) and then 10 μl was mixed with an equal volume of buffer B (500 μM [γ-$^{32}$P] ATP (10 μCi; Amersham Pharmacia Biotech), 25 mM MgCl$_2$, 15 mM 2-(N-morpholine)ethansulfonic acid, pH 6.8). This mixture was added to 30 μl of adipocyte lysate and incubated for 5 min at room temperature. The kinase reaction was stopped by adding 80 μl of 1 N HCl. A mixture of chloroform and ethanol (1:1, 160 μl) was added to the reaction mixture followed by centrifugation at full speed in a microcentrifuge for 2 min, and 40 μl of the organic phase was extracted. The organic phase was spotted on aluminum-backed silica gel 60 thin layer chromatography (TLC) plates that were pre-soaked in developing solvent (chloroform:methanol:2.2 M NH$_4$OH, 9:7:2), run for 3 h in a TLC chamber with the developing solvent, and air-dried. The amount of phosphoinositides was detected by autoradiography.

In result, when PI3-kinase activity in DHH105-treated adipocytes was examined by measuring the conversion of PI to phosphoinositide 3,4,5-triphosphate, it was found that DHH105 treatment significantly increased PI3-kinase activity (FIG. 7A). In FIG. 7A, the intensity of the PIP3 band was normalized with that of PI, and the relative amount of PIP3 was calculated by (normalized band intensity of sample)/(normalized band intensity of control) (lower panel). Data are means±SEM of three independent experiments.

When adipocytes were treated with DHH105 in the presence of PI3-kinase inhibitors, LY294002 (50 μM) or wortmannin (100 nM) and glucose uptake was measured, to determine whether PI3-kinase is involved in DHH105-induced glucose transport, it was found that treatment with LY294002 or wortmannin reduced glucose uptake induced by DHH105 to the level of basal glucose uptake (FIG. 7B). These results indicate that the PI3-kinase pathway is involved in DHH105-induced glucose transport in adipocytes.

When the phosphorylation of Akt/PKB was examined in DHH105-treated adipocytes, to determine whether DHH105 treatment activates Akt/PKB, it was found that DHH105 treatment did not change the amount of Akt/PKB protein, but significantly increased the phosphorylated Akt/PKB as compared with the untreated control adipocytes (FIG. 7C). These results suggest that DHH105 activates Akt/PKB in adipocytes.

The invention claimed is:

1. Isolated 3,4-dihydroxyhydrocinnamic acid naphthalene methyl ester represented by the following formula I:

2. A method for preparing 3,4-dihydroxyhydrocinnamic acid naphthalene methyl ester according to claim 1, comprising reacting 3,4-dihydroxyhydrocinnamic acid with 1-(chloromethyl)naphthalene in the presence of NaHCO$_3$ and KI in N,N-dimethylformamide to produce 3,4-dihydroxyhydrocinnamic acid naphthalene methyl ester, and purifying the 3,4-dihydroxyhydrocinnamic acid naphthalene methyl ester.

3. A pharmaceutical composition for treatment of type 2 diabetes comprising an effective amount of 3,4-dihydroxyhydrocinnamic acid naphthalene methyl ester or a pharmaceutically acceptable salt thereof according to claim 1 as an active ingredient.

* * * * *